(12) United States Patent
Klemm (10) Patent No.: US 11,298,469 B2
(45) Date of Patent: Apr. 12, 2022

(54) MEDICAMENT DELIVERY DEVICE

(71) Applicant: Sanofi-Aventis Deutschland GMBH, Frankfurt am Main (DE)

(72) Inventor: Thomas Klemm, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 247 days.

(21) Appl. No.: 16/346,248

(22) PCT Filed: Oct. 23, 2017

(86) PCT No.: PCT/EP2017/077020
§ 371 (c)(1),
(2) Date: Apr. 30, 2019

(87) PCT Pub. No.: WO2018/082957
PCT Pub. Date: May 11, 2018

(65) Prior Publication Data
US 2020/0046913 A1    Feb. 13, 2020

(30) Foreign Application Priority Data
Nov. 1, 2016  (EP) .................................... 16196752

(51) Int. Cl.
*A61M 5/42* (2006.01)
*A61M 5/32* (2006.01)
*A61M 37/00* (2006.01)

(52) U.S. Cl.
CPC .......... *A61M 5/422* (2013.01); *A61M 5/3298* (2013.01); *A61M 37/0015* (2013.01);
(Continued)

(58) Field of Classification Search
CPC ................ A61M 5/422; A61M 5/3298; A61M 37/0015; A61M 2037/0023–0061
See application file for complete search history.

(56) References Cited

U.S. PATENT DOCUMENTS 6,312,412 B1 * 11/2001 Saied ...................... A61M 5/20
604/191
2002/0013602 A1    1/2002 Huttner
(Continued)

FOREIGN PATENT DOCUMENTS

| CN | 1658792 | 8/2005 |
|---|---|---|
| CN | 102202709 | 9/2011 |

(Continued)

OTHER PUBLICATIONS

International Preliminary Report on Patentability in International Application No. PCT/EP2017/077020, dated May 7, 2019, 6 pages.
(Continued)

*Primary Examiner* — Nathan R Price
*Assistant Examiner* — Courtney B Fredrickson
(74) *Attorney, Agent, or Firm* — Fish & Richardson P.C.

(57) ABSTRACT

A medicament delivery device includes a main injection needle for injecting a medicament into the body of a patient. The medicament delivery device includes a pain reduction device for releasing a pain reduction agent into the body of the patient prior the medicament injection. The pain reduction device includes an array of microneedles.

15 Claims, 3 Drawing Sheets

(52) U.S. Cl.
CPC .............. *A61M 2037/0023* (2013.01); *A61M 2202/048* (2013.01); *A61M 2205/0205* (2013.01); *A61M 2205/0238* (2013.01)

(56) References Cited

U.S. PATENT DOCUMENTS

| | | | |
|---|---|---|---|
| 2004/0138622 A1* | 7/2004 | Palasis | A61B 17/3207 604/173 |
| 2005/0054981 A1 | 3/2005 | Romano | |
| 2005/0177071 A1 | 8/2005 | Nakayama et al. | |
| 2008/0312610 A1* | 12/2008 | Binks | A61P 29/00 604/272 |
| 2009/0326441 A1* | 12/2009 | Iliescu | A61M 37/0092 604/22 |
| 2010/0022965 A1 | 1/2010 | Salzman | |
| 2012/0123387 A1* | 5/2012 | Gonzalez | A61M 5/2033 604/506 |
| 2013/0281932 A1 | 10/2013 | Harish et al. | |
| 2013/0338586 A1 | 12/2013 | Dickinson et al. | |
| 2013/0345638 A1* | 12/2013 | Heidenreich | A61M 37/0015 604/173 |
| 2014/0074025 A1 | 3/2014 | Marti | |
| 2014/0112921 A1* | 4/2014 | Ross | A61K 9/0021 424/134.1 |
| 2015/0051545 A1* | 2/2015 | Henderson | A61M 5/422 604/112 |
| 2016/0271341 A1 | 9/2016 | Chanie et al. | |
| 2017/0182300 A1* | 6/2017 | Kulkarni | A61M 5/14248 |

FOREIGN PATENT DOCUMENTS

| | | |
|---|---|---|
| CN | 103079634 | 5/2013 |
| CN | 104203318 | 12/2014 |
| CN | 105013049 | 11/2015 |
| CN | 105979992 | 9/2016 |
| EP | 2886148 | 6/2015 |
| JP | 2002-172169 | 6/2002 |
| JP | 2015-510802 | 4/2015 |
| JP | 2016-521585 | 7/2016 |
| WO | WO 2011/040900 | 4/2011 |
| WO | WO 2011/115602 | 9/2011 |
| WO | WO 2013/136327 | 9/2013 |
| WO | WO 2013/139850 | 9/2013 |
| WO | WO 2014/193729 | 12/2014 |
| WO | WO 2015/071390 | 5/2015 |

OTHER PUBLICATIONS

International Search Report and Written Opinion in International Application No. PCT/EP2017/077020, dated Feb. 12, 2018, 8 pages.

* cited by examiner

MEDICAMENT DELIVERY DEVICE

CROSS REFERENCE TO RELATED APPLICATIONS

The present application is the national stage entry of International Patent Application No. PCT/EP2017/077020, filed on Oct. 23, 2017, and claims priority to Application No. EP 16196752.6, filed on Nov. 1, 2016, the disclosures of which are incorporated herein by reference.

TECHNICAL FIELD

The present disclosure relates to a device for delivery of medicament to a patient.

BACKGROUND

Medicament injection devices such as auto-injectors are a common type of medicament delivery devices designed to deliver a medicament by injection. This type of devices are designed to be easy to use and intended for self-administration by patients, or administration by persons having no formal medical training.

Auto-injectors typically comprise a syringe pre-filled with medicament and an injection needle fixed to the body of the syringe. One common problem with this type of devices is that the introduction of the injection needle into the skin can be painful for the patient, in particular for a child.

SUMMARY

The present disclosure sets out to provide a device for delivery of medicament which, at least in certain embodiments, reduces the pain induced by the introduction of the injection needle into the skin of the patient.

Aspects of the present disclosure relate to a medicament delivery device.

According to a further aspect, there is provided a medicament delivery device comprising a main injection needle for injecting a medicament into the body of a patient, and a pain reduction device for releasing a pain reduction agent into the body of the patient prior the medicament injection. This may advantageously reduce discomfort to the patient during medicament administration.

The pain reduction device comprises an array of microneedles. This may advantageously help towards providing a pain reduction agent over an area of the skin, and may also reduce discomfort to the patient.

The array of microneedles may be movable between a retracted position in which each microneedle is at least partially retracted in the device, and a deployed position in which a proximal end of each microneedle protrudes from the device. This may provide a safety benefit of helping towards preventing accidental piecing of skin by the microneedles when the device is not in use, and/or may help protect the microneedle array from damage before or after use.

The medicament delivery device may comprise an activation mechanism configured to trigger the release of the pain reduction agent prior to triggering the injection of medicament. This may advantageously help towards ensuring correct operation of the device in the correct sequence, and provide usability benefits of ease of use by a patient, and avoid incorrect use of the device.

The activation mechanism may be configured to drive the array of microneedles between the retracted position and the deployed position.

The main injection needle may be movable between a storage position in which the main injection needle is at least partially retracted in the device, and a use position in which a proximal end of the main injection needle protrudes from the device, and wherein the activation mechanism is configured to drive the array of microneedles from the retracted position towards the deployed position prior driving the main injection needle from the storage position towards the use position.

The pain reduction device may comprise a chamber for storing the pain reduction agent. This may advantageously help towards ensuring an adequate supply of pain reduction agent is available in the device.

The pain reduction device may comprise a coating of pain reduction agent disposed on the surface of the array of microneedles. This may advantageously help towards simplifying configuration and construction of the device, as the pain reduction agent may be pre-applied to the microneedles.

The array of microneedles may comprise between around 70 and around 7000 microneedles.

The array of microneedles may be substantially circular and may have a diameter comprising between around 10 and around 30 millimeters. This may advantageously help towards ensuring an area of the patient's skin around the injection site is sufficiently provided with pain reduction agent.

Each microneedle may have a length within the range of around 0.2 to around 3 millimeters. Each microneedle may have a circular cross-section and may have a diameter ranging between around 40 and around 150 micrometres.

The pain reduction device may comprise a coating including an anti-microbial agent.

The microneedles may comprise hollow microneedles, or may alternatively, or in addition, comprise solid microneedles.

The pain reduction agent may include at least one of an anaesthetic and a locally-acting narcotic agent.

Aspects of the present disclosure also provide a medicament delivery device as described above, comprising a cartridge or other reservoir of medicament.

The medicament delivery device may comprise an auto-injector.

Aspects of the present disclosure also provide a method of reducing pain during a medicament injection, comprising using a medicament delivery device comprising a main injection needle for injecting a medicament into the body of a patient, and a pain reduction device for injecting a pain reduction agent into the body of the patient prior the medicament injection.

The terms "drug" or "medicament" which are used interchangeably herein, mean a pharmaceutical formulation that includes at least one pharmaceutically active compound.

The term "medicament delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems.

BRIEF DESCRIPTION OF THE FIGURES

Exemplary embodiments are described with reference to the accompanying drawings, in which.

DETAILED DESCRIPTION

Certain embodiments provide a medicament delivery device comprising a main injection needle for injecting a medicament into the body of a patient, and a pain reduction device for releasing a pain reduction agent into the body of the patient prior the medicament injection. Providing such a pain reduction device allows to release a pain reducing agent into the injection site prior the medicament injection, and thereby allows to reduce the pain or discomfort felt by the patient when the main injection needle is triggered and inserted through the skin of the patient.

Figure 1A:
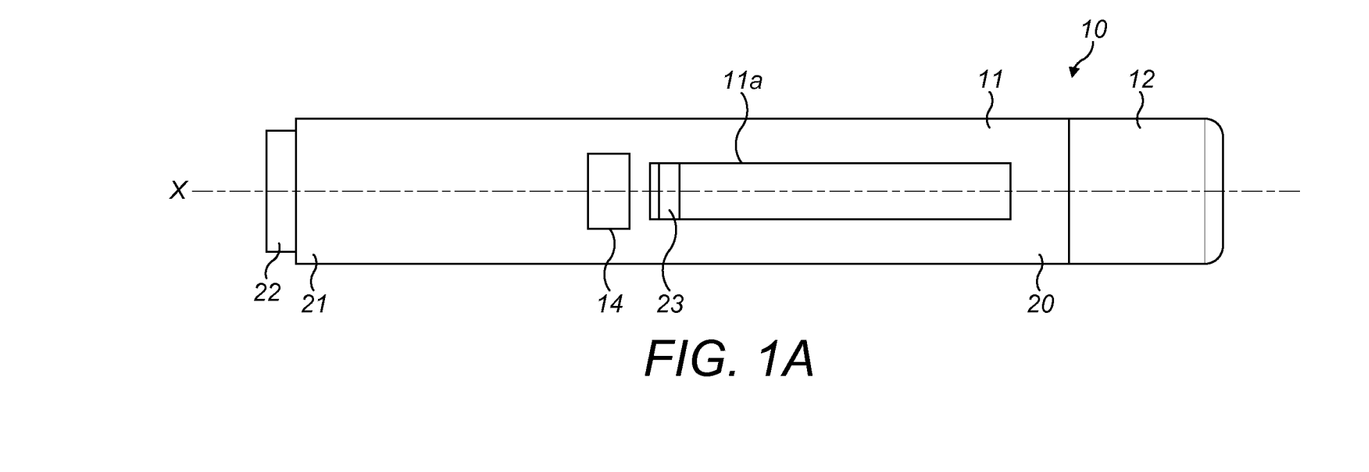
FIGS. 1A and 1B show schematic side views of a medicament delivery device, according to certain embodiments.
Figure 1B:
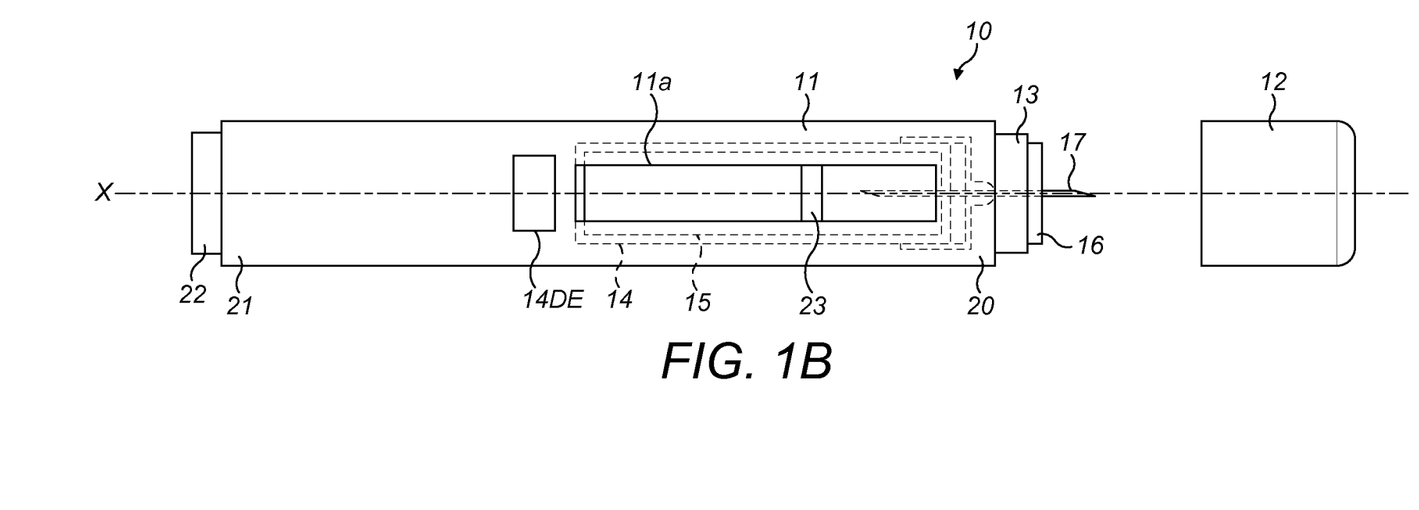

According to some embodiments of the present disclosure, an exemplary drug delivery device 10, herein simply referred to as "device 10", is shown in FIGS. 1A & 1B.

In the context of this application, the terms "proximal" and "distal" herein respectively refer to as relatively closer to the patient and relatively further away from the patient.

The drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Device 10, as described above, is configured to inject a medicament, e.g. a liquid medicament, into a patient's body. Device 10 includes a body or housing 11 which typically contains a reservoir containing the medicament to be injected (e.g., a syringe or a cartridge) and the components required to facilitate one or more steps of the delivery process. Device 10 can also include a cap assembly 12 that can be detachably mounted to the housing 11. Typically a user must remove the cap assembly 12 from the housing 11 before the device 10 can be operated.

The device 10 includes a cartridge 15 pre-filled with liquid medicament, and a pen needle or needle assembly comprising a main injection needle 17 for injecting medicament from the cartridge 15 to a patient's body. The housing 11 includes a window 11a, through which the contents of the cartridge 15 can be viewed.

The device 10 comprises a pain reduction device 16 (shown in more detail in FIG. 2A) for injecting a pain reduction agent into the patient's body prior the medicament injection.

The device 10 also comprises an activation mechanism 14 for controlling the pain reduction agent and medicament injection process.

As shown, the housing 11 is substantially cylindrical and has a substantially constant diameter along a longitudinal axis X. The housing 11 has a proximal region 20 and a distal region 21. The term "proximal" refers to a location that is relatively closer to the site of injection, and the term "distal" refers to a location that is relatively further away from the injection site.

The device 10 can also include a needle sleeve 13 coupled to housing 11 to permit movement of sleeve 13 relative to housing 11. The sleeve 13 is retractably mounted in the housing 11. For example, sleeve 13 can move in a longitudinal direction parallel to longitudinal axis X. Specifically, movement of the sleeve 13 in a distal direction can permit the main injection needle 17 to extend from the proximal region 20 of the housing 11.

Insertion of the main needle 17 can occur via several mechanisms. For example, the main needle 17 may be fixedly located relative to housing 11 and initially be located within an extended needle sleeve 13. Distal movement of the sleeve 13 by placing a proximal end of the sleeve 13 against a patient's body and moving the housing 11 in a proximal direction will uncover the proximal end of the main needle 17. Such relative movement allows the proximal end of the main needle 17 to extend into the patient's body. Such insertion is termed "manual" insertion as the main needle 17 is manually inserted via the patient's manual movement of the housing 11 relative to the sleeve 13.

Another form of insertion is "automated," whereby the main needle 17 moves relative to housing 11. Such insertion can be triggered by movement of sleeve 13 or by another form of activation, such as, for example, a button 22. As shown in FIGS. 1A & 1B, the button 22 is located at a distal end of housing 11. However, in other embodiments, button 22 could be located on a side of housing 11.

Other manual or automated features can include drug injection or needle retraction, or both. Injection is the process by which a bung or piston 23 is moved from a distal location within a cartridge to a more proximal location within the cartridge in order to force a medicament from the cartridge through the main needle 17. In some embodiments, a drive spring (not shown) is under compression before device 10 is activated. A distal end of the drive spring can be fixed within the distal region 21 of housing 11, and a proximal end of the drive spring can be configured to apply a compressive force to a distal surface of piston 23. Following activation, at least part of the energy stored in the drive spring can be applied to the distal surface of piston 23. This compressive force can act on piston 23 to move it in a proximal direction. Such proximal movement acts to compress the liquid medicament within the cartridge, forcing it out of the main needle 17.

Following injection, the main needle 17 can be retracted within sleeve 13 or housing 11. Retraction can occur when sleeve 13 moves proximally as a user removes device 10 from a patient's body. This can occur as the main needle 17 remains fixedly located relative to housing 11. Once a proximal end of sleeve 13 has moved past a proximal end of the main needle 17, and the main needle 17 is covered, sleeve 13 can be locked. Such locking can include locking any distal movement of sleeve 13 relative to housing 11.

Another form of needle retraction can occur if the main needle 17 is moved relative to housing 11. Such movement can occur if the cartridge within housing 11 is moved in a distal direction relative to housing 11. This distal movement can be achieved by using a retraction spring (not shown), located in proximal region 20. A compressed retraction spring, when activated, can supply sufficient force to the cartridge to move it in a distal direction. Following sufficient retraction, any relative movement between the main needle 17 and housing 11 can be locked with a locking mechanism. In addition, button 22 or other components of device 10 can be locked as required.

In the embodiment described herein, the main needle 17 is movable relative to the housing 11 between a storage position and a use position. In the storage position, the main needle 17 is at least partially retracted within the housing 11. In the use position, a proximal end of the main needle 17 protrudes from the proximal region 20 of the housing 11. To expel the medicament from the device 10, the piston 23 is driven from a distal location within a cartridge 15 to a more proximal location within the cartridge 15 so that the medicament is forced from the cartridge 15 through the main needle 17.

Figure 2A:
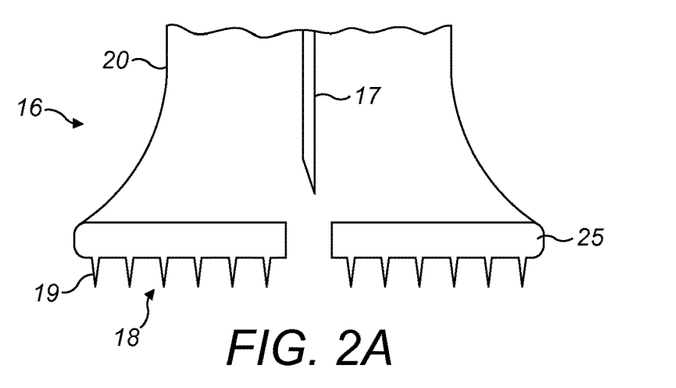
FIG. 2A shows a schematic cross-sectional view of a part of the medicament delivery device of FIG. 1A, the main injection needle being in a storage position, the array of microneedles being in a deployed position.

The pain reduction device 16 is located in the proximal region 20 of the device 10. The pain reduction device 16 comprises a pain reduction agent compartment or chamber 25 for storing the pain reduction agent. The pain reduction device 16 comprises an array 18 including a plurality of hollow microneedles 19 connected to the chamber 25 and through which the pain reduction agent may be expelled. The microneedles 19 are in fluid communication with the chamber 25.

In the present embodiment, the pain reduction device 16 is integrally formed with the device 10. Alternatively, the pain reduction device 16 may be removably connected to the device 10.

The pain reduction agent may be, for example, a locally-acting narcotic or a local anaesthetic agent. Examples of pain reduction agents may include articaine, a combination of basic bismuth gallate and lidocaine, a combination of benzethonium chloride, urea, and polidocanol, benzocaine, a combination of benzocaine and cetylpyridinium chloride, a combination of benzocaine and chlorhexidine, a combination of bufexamac, basic bismuth gallate and lidocaine, bupivacaine, a combination of cetylpyridinium chloride and benzocaine, a combination of cetylpyridinium chloride, dequalinium chloride and lidocaine, cinchocaine, a combination of fluocortolone and lidocaine, a combination of chamomile flowers and lidocaine, lidocaine, a combination of lidocaine and prilocaine, mepivacaine, a combination of oxetacaine, aluminium hydroxide and magnesium hydroxide, a combination of phenazone and procaine, a combination of policresulen and cinchocaine, polidocanol, a combination of polidocanol and hexylresorcinol, prilocaine, procaine, quinisocaine, ropivacaine, a combination of tyrothricin, cetrimonium bromide and lidocaine, or combinations thereof.

In the embodiment described herein, the microneedles 19 are substantially identical to each other. The length of an individual microneedle 19 is comprised within the range of around 0.2 to around 3 millimeters. The length of each microneedle 19 depends on the material of the microneedle and/or on the pain reduction agent used. In the embodiment described herein, each microneedle 19 is made of steel. In the embodiment described herein, each microneedle 19 is at least partially substantially cylindrical. In particular, each microneedle 19 has a circular cross-section and has a diameter ranging between around 40 and around 150 micrometres. The diameter of each microneedle 19 also depends on the material of the microneedle and/or on the pain reduction agent used. It should be noted that the scope of the present invention is not intended to be limited to this particular type of microneedles. For example, the microneedles 19 may have a different shape, such as a conical, tubular or pyramidal shape. In an alternative embodiment, the array 18 comprises a mixture of different microneedles. For instance, the array 18 may include microneedles having various lengths, diameters or shapes.

The array 18 of microneedles 19 may be substantially circular and may have a diameter comprised between around 10 and around 30 millimeters. The array 18 of microneedles 19 may comprise between around 70 and around 7000 microneedles. For example, in the present embodiment, the array 18 has a diameter of around 30 millimeters and comprises around 10 microneedles per millimeter. The number of microneedles 19 of the array 18 in the embodiment described herein therefore comprises around 7000 microneedles. In a variant, the array 18 has a diameter of around 10 millimeters and comprises around 1 microneedle per millimeter. The number of microneedles 19 of the array 18 in this variant is therefore comprised between around 70 to 80 microneedles. The distance between two consecutive microneedles 19 is around one to three times greater that the diameter of each microneedle 19. The distance between two consecutive microneedles may be comprised between around 40 micrometres and around 1 millimetre, and in particular between around 80 micrometers and around 450 micrometers. In the embodiment described herein, the array 18 has a generally circular shape. However, it should be noted that the scope of the present invention is not intended to be limited to this particular shape for the array 18. For example, the array 18 may be square or rectangular.

The device 10 is sterile packaged. Alternatively, or in addition, the array 18 may be covered with a coating which includes an anti-microbial or sterilizing agent, so that the injection area can be disinfected prior the pain reduction agent injection. In the context of this application, the terms "sterilize", "disinfect" or the like mean that at least some of the microorganisms present on the surface of the skin are killed and/or rendered non-infectious.

The chamber 25 includes a bung which is slidably mounted in the chamber 25. The bung is configured to slide within the chamber 25 to direct the pain reduction agent towards the microneedles 19 and thereby expel the pain reduction agent out of the device 10. Alternatively, the chamber 25 may be made with a flexible material such that when a force is applied to the chamber 25 towards the injection site, the pain reduction agent is expelled out of the chamber 25 through the microneedles 19. In a further alternative embodiment, the chamber 25 comprises a breakable membrane or film. In use, the chamber 25 gets pressurized and the breakable film breaks so that the pain reduction agent can flow through the hollow microneedles 19. In a still further alternative embodiment, the chamber 25 is made with a soft material and in use, the main needle 17 pierces the chamber 25 so that the pain reduction agent can be released towards the micro-needles 19.

Figure 2B:
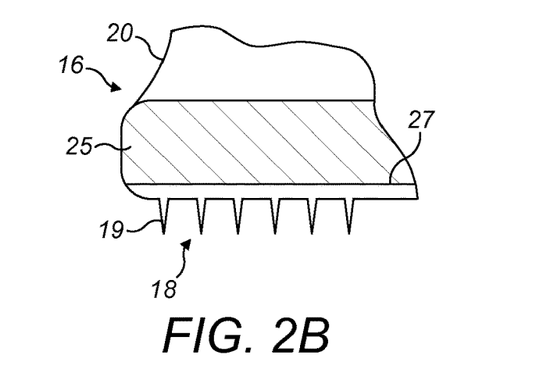
FIG. 2B shows a detail of FIG. 2A.
Figure 2C:
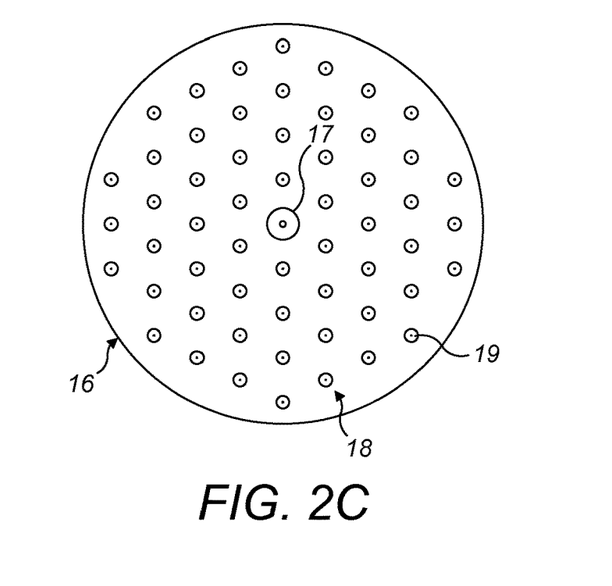
FIG. 2C shows a bottom view of the medicament delivery device of FIG. 2A.

As shown in FIG. 2B, a permeable membrane such as a pressure sensitive membrane 27 may be provided between the chamber 25 and the hollow microneedles 19 to retain the pain reduction agent prior injection of the pain reduction agent. In use, the pain reduction agent may flow through the membrane 27 in various ways, for example by diffusion and/or hydrodynamically. When the pain reduction agent flows by diffusion, the pain reduction agent is first dissolved in the membrane 27. A gradient of chemical potential between the chamber 25 and the membrane 27 ensures the diffusion of the pain reduction agent from the chamber 25 towards the membrane 27, until the chemical potentials in the chamber 25 and in the membrane 27 become equal, i.e. until the equilibrium is reached at the interface between the chamber 25 and the membrane 27. The pain reduction agent may also flow hydrodynamically or by convection towards the membrane 27. The membrane 27 may be a membrane of the type used in micro-filtration and/or ultra-filtration, such as membranes used to separate macromolecules from a solution, colloids from a dispersion or to remove bacteria. During this process, the pain reduction agent particles or molecules retained on the membrane 27 form a pulpy mass or filter cake on the membrane 27. This blockage of the membrane 27 may hamper the filtration and the flow of pain reduction agent towards the microneedles 19. This blockage can be reduced by the use of cross-flow filtration, where the pain reduction agent flows tangentially along the front of the membrane 27 at positive pressure relative to the permeate side or back of the membrane 27. A proportion of pain reduction agent particles which are smaller than the membrane pore size passes through the membrane 27 as permeate or filtrate, and the remainder is retained on the front of the membrane 27 as retentate. The tangential flow on the front creates a shear stress that cracks the filter cake and reduces the fouling.

The array 18 is arranged relative to the housing 11 so that the proximal end of the microneedles 19 protrude from the device 10, and so that once the device 10 is placed on the injection area, the microneedles 19 penetrate the skin and/or an internal tissue and/or a wall of a vessel of the patient. In the present embodiment, the array 18 is arranged in the device 10 such that the microneedles 19 adopt at least two different positions relative to the housing 11. Specifically, the array 18 is movable relative to the housing 11 between a retracted position and a deployed position. In the retracted position, the array 18 is retracted in the device 10, i.e. the microneedles 19 are at least partially retracted within the housing 11. In the deployed position, the array 18 protrudes from the device 10, i.e. the tips of the microneedles 19 protrude from the proximal region 20 of the housing 11. In an alternative embodiment, the array 18 may be fixed relative to the housing 11.

The activation mechanism 14 is disposed in the housing 11. The activation mechanism 14 is configured to drive the main needle 17 between the storage position and the use position and to drive the piston 23 within the cartridge 15. Likewise, the activation mechanism 14 is configured to drive the array 18 between the retracted position and the deployed position, and to drive the bung within the chamber 25. In particular, the activation mechanism 14 is configured to drive the array 18 from the retracted position towards the deployed position prior driving the main needle 17 from the storage position towards the use position, so that the pain reduction agent is injected to the patient's body prior the medicament injection. The activation mechanism 14 is adapted to drive the main needle 17 at the end of a predetermined period of time after that the pain reduction agent has been injected into the patient's body. For example, the period of time between the end of the pain reduction agent injection and the triggering of the main needle 17 is comprised between one or more second and 1 minute depending on the skin type, the location of the injection site in the body, the medicament and/or the pressure of the medicament. To this end, the activation mechanism 14 may include a timer configured to delay the triggering of the main needle 17 for a predetermined time after the pain reduction agent injection. This may provide sufficient time for the pain reduction agent to take effect in the patient's body, for example to anesthetise the injection site, prior the medicament injection. The activation mechanism 14 is triggered by pressing the button 22.

The operation of the medicament injection device 10 in accordance with certain embodiments will now be described.

Initially, the main needle 17 is in the storage position, i.e. the main needle 17 is retracted within the housing 11. The array 18 is in the retracted position, i.e. the tips of the microneedles 19 are retracted within the housing 11.

In use, the cap assembly 12 is pulled away from the housing 11, and the device 10 is placed onto the patient's skin, on the injection site. Then, the button 22 is pressed and the activation mechanism 14 is triggered. The activation mechanism 14 drives the array 18 so that the array 18 moves from the retracted position towards the deployed position. While the array 18 moves towards the deployed position, the microneedles 19 move towards the injection site until the microneedles 19 reach and penetrate the skin of the patient. The sterilizing coating covering the array 18 disinfects the injection area prior the pain reduction agent injection. Then, the activation mechanism 14 drives the bung which slides within the chamber 25 towards the proximal extremity of the device 10 to expel the pain reduction agent through the membrane 27 and through the microneedles 19 into the patient's body, for example into the skin and/or an internal tissue and/or a wall of a vessel of the patient.

Once the pain reduction agent injection has been performed and the injection area is numbed, the activation mechanism 14 drives the array 18 back towards the retracted position so that the microneedles 19 move away from the injection site. Then, after a predetermined period of time, the activation mechanism drives the main needle 17 from the storage position towards the use position. The main needle 17 moves towards the injection site until the main needle 17 reaches and penetrates the patient's skin. Since the injection site has been numbed by the pain reduction agent, the pain felt by the patient when the main needle 17 penetrates the skin is reduced. The activation mechanism 14 then drives the piston 22 towards the proximal region 20 of the device 10 to expel the medicament through the main needle 17. The medicament is then injected to the patient in a well-known manner. After the injection, the activation mechanism 14 drives the main needle 17 back towards the storage position so that the main needle 17 moves away from the injection site. The device 10 may then be discarded or prepared for a future use.

Figure 3A:
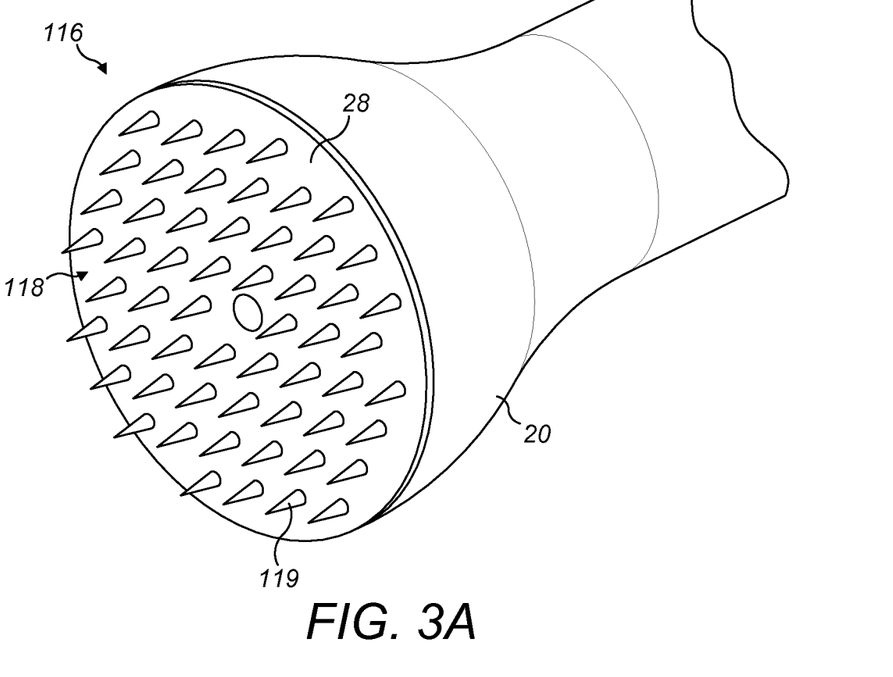
FIGS. 3A and 3B show respectively a schematic perspective view and a schematic cross-sectional view of a medicament delivery device according to a further embodiment.
Figure 3B:
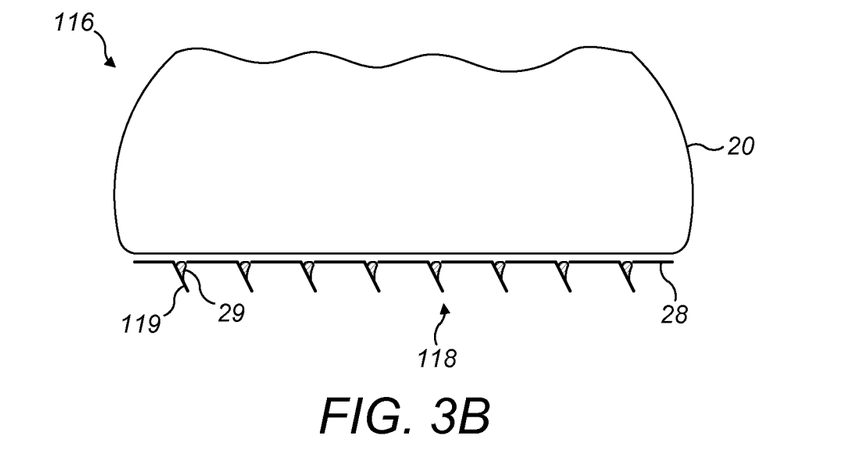

A further embodiment is depicted in FIGS. 3A and 3B. Like features retain the same reference numerals and a detailed description of such like features will not be repeated.

In the further embodiment, the device 110 comprises a foil or metal sheet 28 on which is disposed an array 118 of microneedles 119. The surface of the microneedles 119 is covered with a coating 29 of pain reduction agent. The coating 29 may include a highly concentrated anaesthetic cream or ointment. The array 118 can be prepared in various ways. For example, the array 118 can be thermoformed or made from deep-drawn metal, or can be made from hard plastic. The coating 29 of pain reduction agent can be drizzled on the microneedles 119 and/or between the microneedles 119, on the surface of the metal sheet 28. The microneedles 119 may be solid microneedles 119. Alternatively, the microneedles 119 may be hollow microneedles 119 prefilled with the pain reduction agent.

In the embodiments described above, the medicament delivery device is described as being an auto-injector. However, the scope of the invention is not intended to be limited to this particular type of medicament delivery device and other types of devices are intended to fall within the scope of the invention, for example a patch pump device.

In the embodiments described above, the medicament delivery device is described as comprising a pain reduction device including an array of microneedles. However, the scope of the invention is not intended to be limited to this particular type of medicament delivery device and other types of devices are intended to fall within the scope of the invention, for example a device in which the pain reduction device includes a supplementary injection needle for preliminary injection of the pain reduction agent prior the medicament injection.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament delivery device comprising:
 a main injection needle for injecting a medicament into a body of a patient;
 a pain reduction device for releasing a pain reduction agent into the body of the patient prior to injection of the medicament, wherein the pain reduction device comprises an array of microneedles, and wherein the main injection needle is extendable through the array of microneedles; and
 an activation mechanism configured to trigger the release of the pain reduction agent prior to triggering the injection of the medicament, wherein the main injection needle is movable between a storage position in which the main injection needle is at least partially retracted in the device, and a use position in which a proximal end of the main injection needle protrudes from the device, and wherein the activation mechanism is configured to drive the array of microneedles from a retracted position towards a deployed position prior to driving the main injection needle from the storage position towards the use position.

2. The medicament delivery device according to claim 1, wherein in the retracted position, each microneedle is at least partially retracted in the device, and in the deployed position, a proximal end of each microneedle protrudes from the device.

3. The medicament delivery device according to claim 2, wherein the activation mechanism is configured to trigger the release of the pain reduction agent prior to triggering the injection of the medicament.

4. The medicament delivery device according to claim 1, wherein the pain reduction device comprises a chamber for storing the pain reduction agent.

5. The medicament delivery device according to claim 1, wherein the pain reduction device comprises a coating of the pain reduction agent, the coating disposed on a surface of the array of microneedles.

6. The medicament delivery device according to claim 1, wherein the array of microneedles comprises between 70 and 7000 microneedles.

7. The medicament delivery device according to claim 1, wherein the array of microneedles is substantially circular and has a diameter of between 10 and 30 millimeters.

8. The medicament delivery device according to claim 1, wherein each microneedle has a length between 0.2 and 3 millimeters.

9. The medicament delivery device according to claim 1, wherein each microneedle has a circular cross-section and has a diameter of between 40 and 150 micrometers.

10. The medicament delivery device according to claim 1, wherein the pain reduction agent comprises an anesthetic.

11. The medicament delivery device according to claim 1, wherein the pain reduction agent comprises a locally acting narcotic agent.

12. The medicament delivery device according to claim 11, wherein the pain reduction agent comprises an anesthetic and the locally acting narcotic agent.

13. The medicament delivery device according to claim 1, further comprising a cartridge of the medicament.

14. The medicament delivery device according to claim 1, wherein the medicament delivery device is an auto-injector.

15. The medicament delivery device according to claim 1, wherein the activation mechanism is configured to trigger the release of the pain reduction agent prior to triggering the injection of the medicament.

* * * * *